(12) United States Patent
Sivard et al.

(10) Patent No.: US 8,634,916 B2
(45) Date of Patent: Jan. 21, 2014

(54) HEART STIMULATING DEVICE WITH SELECTING OPTIMAL ELECTRODE CONFIGURATION

(75) Inventors: Ake Sivard, Solna (SE); Anders Lindgren, Taby (SE); Karlsson Andreas, Solna (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/498,888

(22) PCT Filed: Sep. 30, 2009

(86) PCT No.: PCT/SE2009/000431
§ 371 (c)(1),
(2), (4) Date: Mar. 28, 2012

(87) PCT Pub. No.: WO2011/040842
PCT Pub. Date: Apr. 7, 2011

(65) Prior Publication Data
US 2012/0185013 A1 Jul. 19, 2012

(51) Int. Cl.
*A61N 1/365* (2006.01)
(52) U.S. Cl.
USPC .......................................................... 607/25
(58) Field of Classification Search
USPC .......................................................... 607/25
See application file for complete search history.

(56) References Cited

U.S. PATENT DOCUMENTS

| 5,243,981 | A | 9/1993 | Hudrlik |
| 5,480,441 | A * | 1/1996 | Hudrlik ........................... 607/17 |
| 6,931,281 | B2 | 8/2005 | Bradley et al. |
| 7,415,307 | B2 * | 8/2008 | Sharma et al. ................. 607/17 |
| 2007/0173897 | A1 | 7/2007 | Zdeblick |
| 2008/0146928 | A1 | 6/2008 | Dala-Krishna |
| 2008/0177344 | A1 | 7/2008 | Maskara et al. |
| 2008/0306567 | A1 | 12/2008 | Park et al. |

* cited by examiner

*Primary Examiner* — George Manuel

(57) ABSTRACT

Heart stimulating device comprising a stimulation pulse generator arranged in a stimulator housing, where the heart stimulating device is coupled to a plurality of stimulation and sensing electrodes arranged at one or many leads, the electrodes being adapted to be arranged in connection with the heart to stimulate the heart. The device further comprises a sensing unit adapted to sense electrical heart tissue responses to applied electrical stimulation pulses via said electrodes. The pulse generator is adapted to generate stimulation pulses to be applied to the heart tissue by different electrodes, and for each of the applied pulses resulting in a depolarization wave in the heart tissue a depolarization wave velocity parameter of the wave is determined by the sensing unit and stored in a memory unit. The stored wave velocity parameters, related to different stimulating electrodes, are compared to each other in a comparison unit and the comparison is used to adapt a stimulation mode when stimulating the heart to optimize the hemodynamic performance of the heart.

20 Claims, 4 Drawing Sheets

HEART STIMULATING DEVICE WITH SELECTING OPTIMAL ELECTRODE CONFIGURATION

FIELD OF THE INVENTION

The present invention relates to a device according to the preamble of the independent claim.

BACKGROUND OF THE INVENTION

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). Heart failure causes diminished pumping power of the heart, resulting in the inability to deliver enough blood to meet the demand of the body tissues. Heart failure may affect the left side of the heart, right side of the heart or both sides of the heart, and may cause weakness, loss of breath, and build up of fluids in the lungs or in other body tissues. For example, HF may, when deterioration of the muscles of the heart, reduce the heart's contractility or synchronism. The reduced contractility decreases the cardiac output and may result in an increased heart rate and enlargement of the heart. In some cases, HF is caused by unsynchronized contractions of the left and right heart chambers. Particularly when the left or right ventricles are affected, the unsynchronized contraction can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers, and the pacing pulses are then delivered to the heart chambers in a sequence that cause the heart chambers to contract in synchrony, increasing the pumping power of the heart and delivering more blood to the tissues of the body. In the case of dysynchrony of right and left ventricular contractions, a biventricular pacing therapy may pace one or both ventricles. Bi-atrial pacing or pacing of all four heart chambers may alternatively be used.

In the following is briefly discussed some patent documents related to optimization of the performance of the heart by use of implantable heart stimulators, and specifically related to CRT.

US-2007/0060961 discloses a method for determining optimal implantation site of an implantable medical lead. Electrical energy is delivered at different sites of the left ventricle to initiate cardiac activation at a plurality of different test locations. A hemodynamic sensor, such as a pressure sensor or blood volume measuring sensor, is used for determining a respective hemodynamic response for the different test sites.

US-2008/177344 relates to the selection of optimal pacing site for CRT with an implantable LV multi-electrode lead. At each of the multiple electrodes in connection with the left ventricle a time parameter equal to the start of a QRS deflection and the peak of the QRS deflection of the LV electrogram is determined.

This time parameter is related to the increase in peak rate of increase of LV pressure. The time parameter should be as large as possible for optimal pacing site with the CRT.

More in detail, in US-2008/177344 the electrode site selection is preferably based on timing interval measurements associated with ventricular depolarization. These timing measurements may be used to identify and/or select electrode site(s) that provide for improved responsiveness to cardiac resynchronization therapy. Electrode sites may be evaluated to identify those that will respond to CRT ("responder sites"), and such identified responder sites may be further evaluated to determine their relative degree of responsiveness to CRT. Responder sites may be characterized by late activation of depolarization and/or prolonged depolarization. Electrode site characterization may be implemented through analysis of a timing interval defined between a first deflection and a maximum deflection of a ventricular depolarization for a given electrode site.

US-2004/0102812 relates to a cardiac rhythm management device adapted to select optimal pacing site for resynchronization therapy. The site selection is based on the relative depolarization times at the sensing/pacing electrode sites during a cardiac contraction. The objective of the therapy is to produce a more coordinated contraction than naturally occurs. This is achieved by selecting the paced site that becomes depolarized later than the other available pacing sites.

Earlier Cardiac Resynchronization Therapy (CRT) systems have only had one lead with two electrodes implanted on the left heart side via the coronary sinus, which means that the pacing vector is limited in flexibility. Even with the newly developed multi (e.g. quadruple) pole electrodes the lack of good optimization systems makes it difficult to take full advantage of the four electrodes available on the left side.

It has been observed that the origin of the pace pulse has large impact on the cardiac performance, this is inter alia due to the fact that scar and/or ischemic tissue may serve as an obstacle for the depolarization wave on its propagation through the heart tissue.

The inventors have realized that this causes the wave front to move much slower and/or is forced to make a detour around the obstacle resulting in a less than optimal heart beat. However, by pacing from a slightly different location the propagation of the depolarization wave may be facilitated and thus improving heart performance. E.g. a quad pole lead offers the possibility to improve the heart performance by selecting which of the four electrodes to pace from. However, so far, no or only limited possibilities are available to guide the physician in the electrode selection during implantation and follow-up as well as when the patient is out of the hospital (automatic optimization).

Thus, the general object of the present invention is to achieve a heart stimulating device adapted to optimize hemodynamic performance of the heart by analysing and monitoring different electrode selections, e.g. for selecting an optimal electrode configuration.

SUMMARY OF THE INVENTION

According to the present invention an optimal pacing site, in particular for an electrode at an LV multi-electrode lead, is selected by measuring a depolarization wave velocity parameter, such as the depolarization wave velocity. The pacing electrode resulting in the highest depolarization wave velocity parameter is selected as the optimal pacing electrode.

Herein, the depolarization wave velocity is generally defined as how fast the depolarization wave is spread in the heart tissue.

According to one embodiment, the present invention enables a heart stimulating device having CRT capability and connected to a multi pole LV lead to automatically choose which one of the electrodes on the left side to pace from in order to achieve optimal hemodynamic performance.

The invention provides such an optimization device by sensing the depolarization wave at the electrodes not involved in the delivering of the pace pulse and from the time difference calculating the average velocity. By selecting different electrodes to pace from and then calculate the conduction time for each electrode, it is easy to select the configuration that resulted in the highest depolarization wave velocity and thus the best electrode to pace from.

One advantage of the present invention is that it gives the physician the ability to optimize the choice of pacing electrodes for a heart stimulating device connected to a multi-pole LV lead. Another advantage is that no extra hardwire is required when implementing the invention, in that the present invention preferably is implemented in software.

The invention is applicable at implantation of the device, at follow-up procedures, and also out of clinic during normal operation of the device.

As will be clearly disclosed herein there are two main advantages of the present invention, firstly to determine an optimal electrode configuration, and secondly to monitor a patient's hemodynamic status. The latter is achieved by monitoring changes of depolarization wave velocities which may be used to detect adverse changes in the patient's hemodynamic status. If velocity changes are monitored then the device may automatically determine if an alternative configuration instead may be used as well as an alarm signal may be generated and transmitted to an external device.

The present invention is also applicable in an external programming device used to communicate and program an implanted heart stimulating device. According to this embodiment parts of, or all, analysis is performed by the external programming device.

Furthermore, in another embodiment of the present invention the heart stimulating device is a pacing system analyzer (PSA) used in connection with implantation of an implantable device.

SHORT DESCRIPTION OF THE APPENDED DRAWINGS

FIG. 1 schematically illustrates one embodiment of the present invention.

DETAILED DESCRIPTION OF PREFERRED EMBODIMENTS OF THE INVENTION

Figure 4:
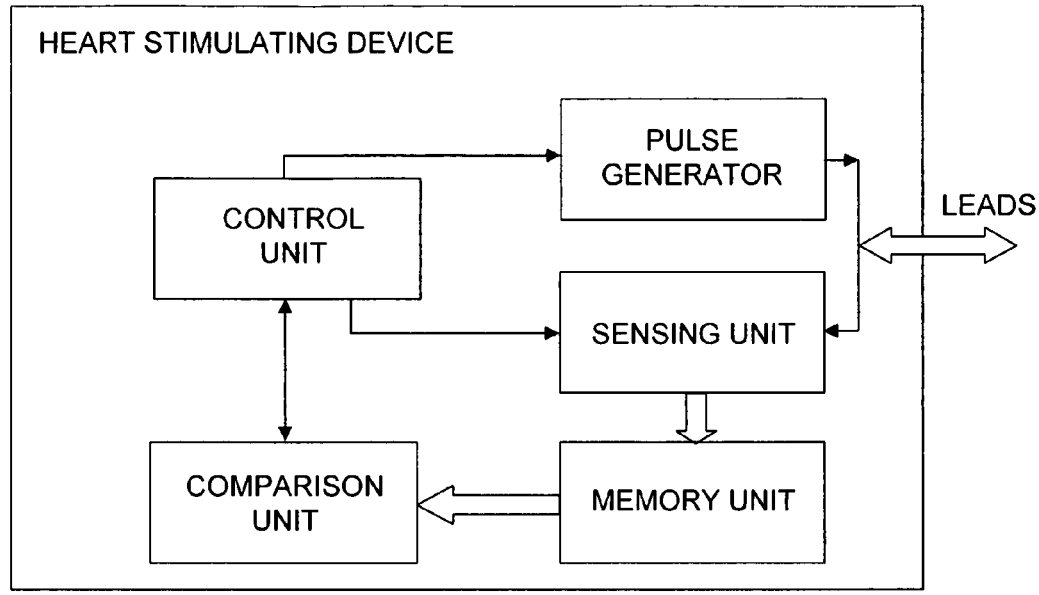
FIG. 4 is a schematic block diagram of the heart stimulating deice according to the present invention.

With references to the figures, in particular FIGS. 1 and 4, the present invention will now be described in detail.

Thus, the present invention relates to a heart stimulating device comprising a stimulation pulse generator arranged in a stimulator housing 2. The heart stimulating device being connectable to a plurality of stimulation and sensing electrodes arranged at one or many electrode leads 3, 4, 13 and the electrodes being adapted to be arranged in connection with the heart 1 to stimulate the heart. This will be described below in detail with reference to FIG. 1.

The device further comprises a sensing unit adapted to sense electrical heart tissue responses to applied electrical stimulation pulses via the electrodes.

The pulse generator is adapted to generate stimulation pulses to be applied to the heart tissue by different electrodes, and for each of the applied pulses resulting in a depolarization wave in the heart tissue a depolarization wave velocity, or a depolarization wave velocity measure, of the wave is determined by the sensing unit and stored in a memory unit.

The stored wave velocities, or velocity measures, related to different stimulating electrodes, are compared to each other in a comparison unit and the comparison is used to adapt the stimulation mode when stimulating the heart to optimize the hemodynamic performance of the heart.

According to one embodiment the stimulation mode is adapted by changing the electrode configuration, which e.g. is achieved, in the unipolar alternative, by using another electrode when applying the stimulation pulses, or in the bipolar alternative, by using another pair of electrodes when applying the stimulation pulses. This will be further discussed below by referring to FIGS. 2 and 3.

Preferably, the electrode, or electrode pair, that provided the highest depolarization wave velocity is chosen in order to adapt the electrode configuration.

According to another embodiment the depolarization wave velocity, or depolarization wave velocity measure, is used to monitor the hemodynamic performance of the heart.

The depolarization wave velocity, or depolarization wave velocity measure, may be used to adapt a heart stimulation mode of the heart stimulating device in dependence thereto. This may preferably be achieved by changing the electrode configuration, but also by changing other parameters related to the stimulation mode, e.g. different time periods used to timely apply the stimulation pulses.

The depolarization wave velocity, or wave velocity measure, is measured at electrodes not used for stimulation, e.g. at electrodes at the same lead, at electrodes at different leads, in relation to an electrode at the housing of the device. As will be further disclosed below the present invention is equally applicable when using unipolar stimulation and sensing, as well as when using bipolar simulation and sensing.

In one embodiment the depolarization wave velocity is measured by determining the distance between the used stimulation electrode and the used sensing electrode and dividing the distance with the time period from applied stimulation until the wave reaches the sensing electrode. If the stimulation and sensing electrodes are at the same lead the distance is normally known in advance as it is related to the longitudinal structure of the lead.

According to another embodiment the wave velocity measure is a time measure determined by measuring the time from applied stimulation until the wave reaches the used sensing electrode.

Preferably, the device being adapted to be connected to a left ventricular multi electrode lead adapted to stimulate the left ventricle of the heart. In FIG. 1 an exemplary left ventricular electrode lead is illustrated which is provided with four electrodes.

The device further comprises a control unit adapted to initiate determination of the optimal electrode configuration at predetermined time intervals, these time intervals may be set by a physician in connection with implantation of the stimulator device, or may be set or altered at follow-up.

One further option, alone or in combination with the above, is that the control unit being adapted to initiate determination of the optimal electrode configuration when receiving an initiation signal, preferably via an external telemetry signal.

The control unit may further be adapted to monitor changes of depolarization wave velocities, or wave velocity measures, which may be used to detect adverse changes in the patient's hemodynamic status. If a monitored velocity change is detected then the device automatically determines if an alternative electrode configuration instead may be used, or an alarm signal may be generated and transmitted to an external device.

Figure 7:
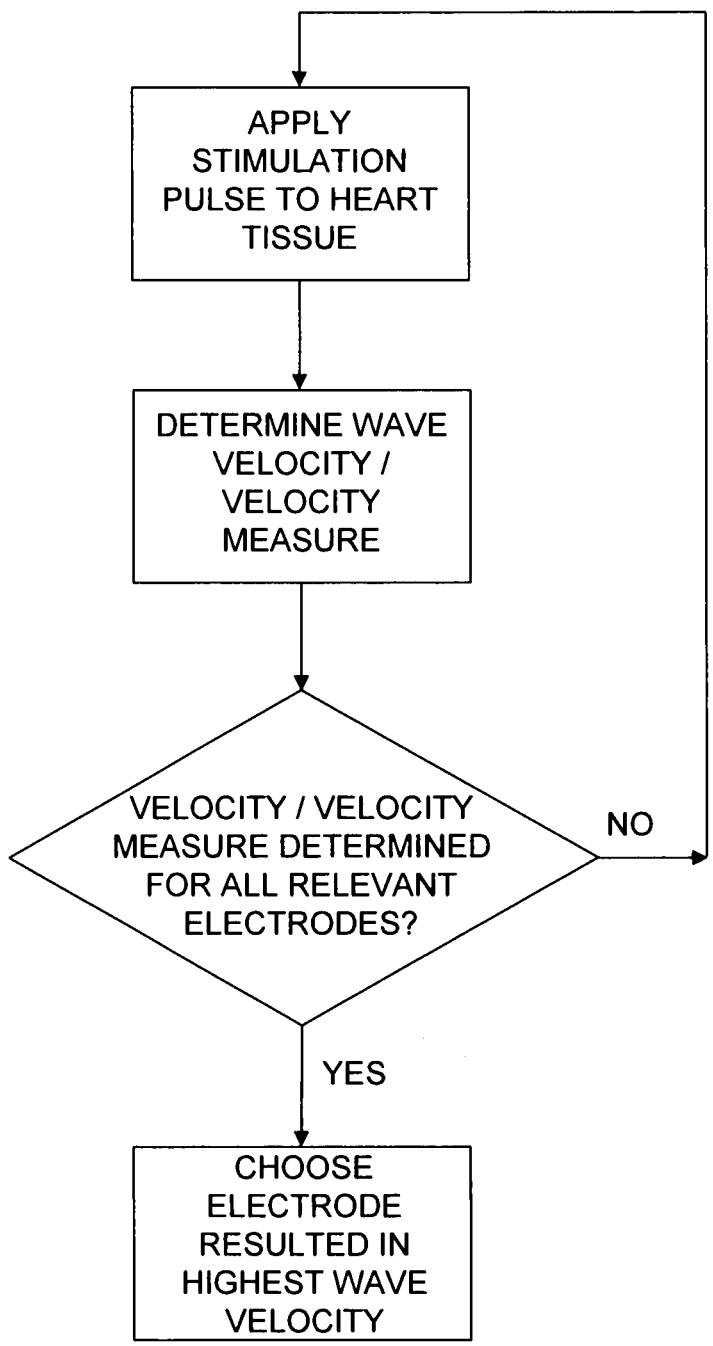
FIG. 7 is a flow-diagram illustrating the present invention.

FIG. 7 is a flow diagram schematically illustrating a test procedure used to choose an optimal electrode configuration.

The procedure is initiated by applying a stimulation pulse to the heart tissue via one of the electrodes to be tested. The wave velocity, or the wave velocity measure, is determined at one or many sensing electrodes, and the determined value is stored in the memory unit. This is repeated until all relevant electrodes are tested, which e.g. could be all LV electrodes. The values obtained during the test procedure is then compared to each other in the comparison unit and the result of the comparison is then evaluated. The result of the evaluation may be that the electrode having the highest wave velocity is chosen to be used when stimulating the heart. In addition the velocity values are stored in the memory unit in a separate history section, in order to be able to perform further evaluation of the values, e.g. at follow up, e.g. in order to identify long-term trends, and/or to identify and further investigate specific wave velocity patterns that may be significant for different physiological states.

Figure 1:
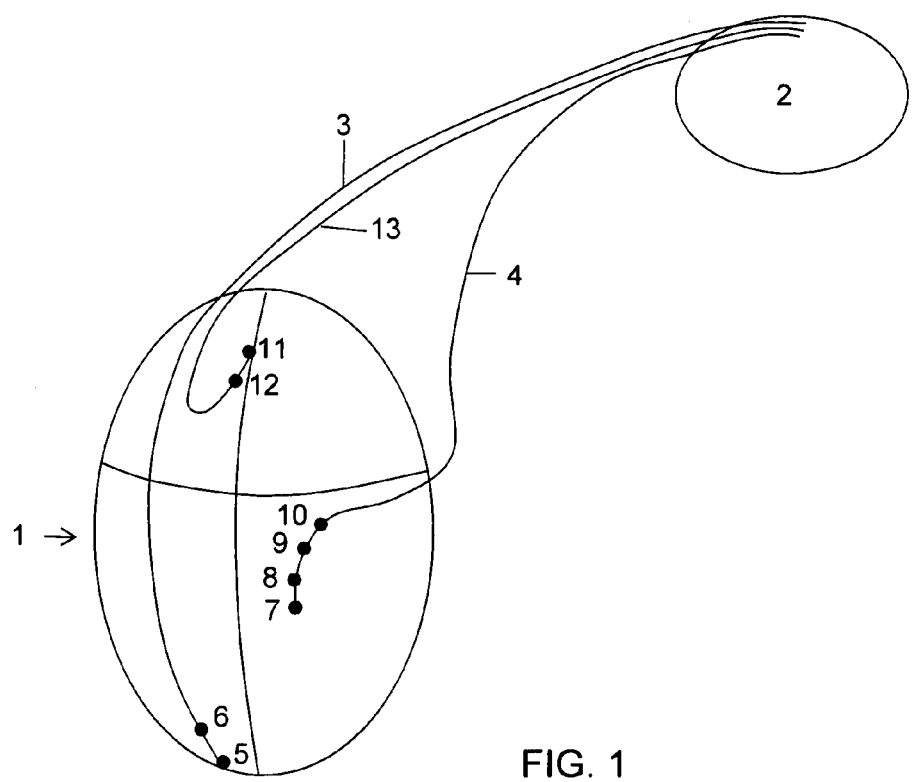

FIG. 1 is a schematic illustration of an exemplary set-up of electrode leads connected to a heart stimulation device according to the present invention.

In the figure is shown the heart stimulating device adapted to stimulate a patient's heart 1 and provided with a housing 2. In the illustrated example three leads are connected to the device, a right ventricular (RV) lead 3, provided with an RV tip electrode 5 and an RV ring electrode 6, a right atrial (RA) lead 13, provided with an RA tip electrode 11 and an RA ring electrode 12, and also a left ventricular (LV) lead 4, that in this example is provided with four electrodes, LV electrodes 7, 8, 9 and 10.

According to a first embodiment the stimulation is performed in a unipolar mode and in order to optimize the pacing electrode configuration each of the LV electrodes is used to pace the heart using the housing 2, RV tip electrode 5 or RV ring electrode 6 as the other node.

Figures 2A, 2B, 2C, 2D:
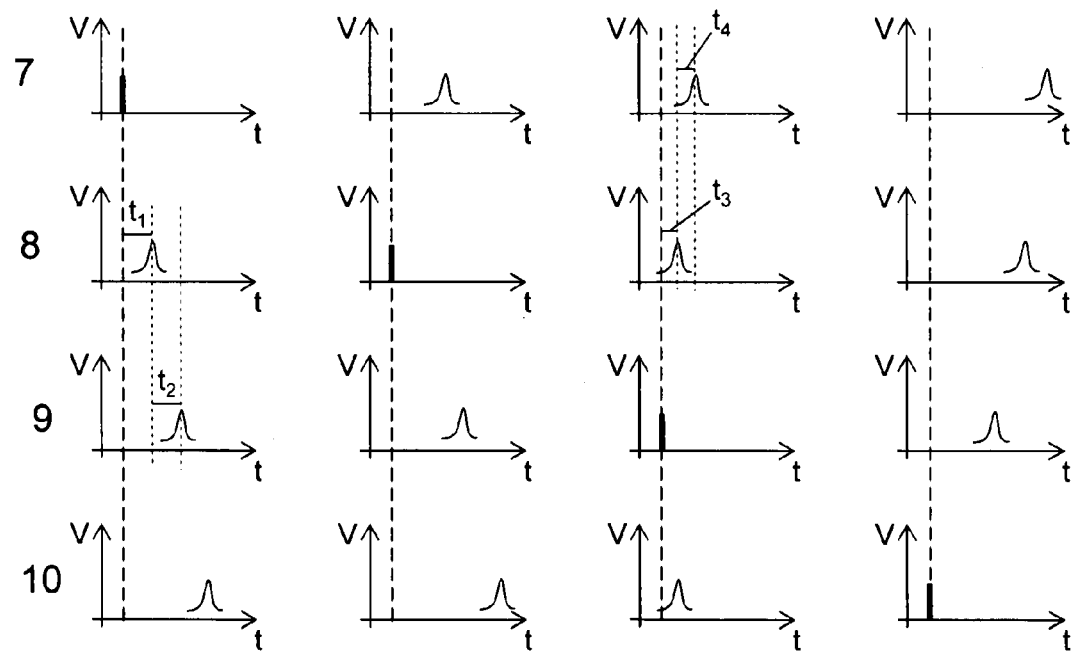
FIGS. 2a-2d show graphs illustrating the timely relationship of applied and sensed events in a unipolar set-up to illustrated the present invention.

FIGS. 2a-2d show schematic graphs for each of the LV electrodes. In the graph the amplitude in Volt is indicated on the Y-axis and time on the X-axis. The stimulation pulse is illustrated by a bold vertical line and the depolarization wave is schematically illustrated. In FIG. 2a LV electrode 7 is used to apply the stimulation pulse, in FIG. 2b LV electrode 8 is used to apply the pulse, in FIG. 2c LV electrode 9 is used, and finally in FIG. 2d LV electrode 10 is used. The upper graphs in FIGS. 2a-2d relate to LV electrode 7, next row of graphs to LV electrode 8, etc.

When e.g. LV electrode 7 to housing 2 is used to pace the left ventricle the depolarization wave passes the other three LV electrodes and may be detected as seen in FIG. 2a.

The important information obtained from the graphs is the relative position of the wave at the different electrodes which is used, inter alia, to determine which of the LV electrodes that results in the highest depolarization wave velocity.

When the measurement procedure is to be performed the control unit triggers the pulse generator to apply a stimulation pulse at a selected electrode. The sensing unit receives sensed depolarization signals from a sensing electrode and the signal is preferably filtered and/or amplified according to known signal processing procedures. The depolarization wave is identified by comparing the received signal to one or many thresholds set at relevant levels chosen in relation to a normal amplitude of a depolarization wave. In an alternative embodiment different pattern recognition methods may be used. When a depolarization wave is identified the time from applied stimulation pulse until the peak of the wave is determined. Naturally other significant parts of the wave curve may be used when determining the time from applied stimulation, e.g. a positive flank above a specified threshold. Then, data identifying the used stimulation electrode, the measured time period, and other relevant data, e.g. a date stamp, is stored in the memory unit. This test procedure is repeated until all relevant electrodes are tested, e.g. all electrodes at the LV lead.

FIG. 2a shows the wave first passing electrode 8, then electrode 9 and electrode 10. Since the distance between the LV electrodes is known the average velocity of the wave may be calculated as the distance between e.g. the LV electrode 7 and the LV electrode 8 divided by the time it takes for the wave to reach LV electrode 8 which is indicated in FIG. 2a as t1, or as the distance between LV electrode 8 and LV electrode 9 divided by the time it takes from the wave passing LV electrode 8 to it reaches LV electrode 9, which is indicated in FIG. 2a as t2.

FIGS. 2b, 2c and 2d show the depolarization wave passing the LV electrodes when pacing with the LV electrode 8 in FIG. 2b, the LV electrode 9 in FIG. 2c and the LV electrode 10 in FIG. 2d, respectively.

In the case of equal distances between the LV electrodes FIGS. 2a-2d show that pacing from LV electrode 9 results in the fastest depolarization wave given by the short time for the wave to reach LV electrode 8 seen as t3 or in the short time difference between the wave passing LV electrode 8 and LV electrode 7 seen as t4.

Therefore, the conclusion is that of all the four different unipolar (in this case the LV-electrode to the device housing) pacing configurations, that is possible, the configuration housing 2 to LV electrode 9 is the optimal one.

Also with references to FIG. 1 a second embodiment, a bipolar LV pacing, of the present invention now will be described in detail.

In this embodiment the heart stimulating device 2 also is adapted to be connected to the patient's heart via the RV lead 3, the RA lead 13 and the LV lead 4.

To optimize the pacing electrode configuration each combination of two out of the four LV electrodes is used to pace the heart during the test procedure. The polarization wave is then sensed, e.g. between the RV tip electrode 5 and the RV ring electrode 6. Naturally other sensing electrode configurations may be used, e.g. between the RA tip electrode 11 and RA ring electrode 12.

Figure 3:
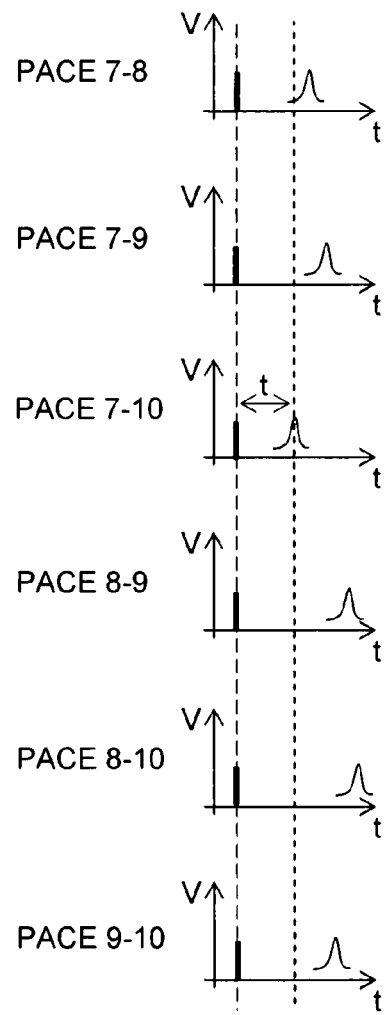
FIG. 3 shows graphs illustrating the timely relationship of applied and sensed events in a bipolar set-up to illustrated the present invention.

FIG. 3 discloses graphs illustrating bipolar pacing according to the second embodiment. The y-axis denotes voltage and the x-axis time. The pace pulse is designated as a bold vertical line and the depolarization wave curve sensed between RV tip electrode 5 and RV ring electrode 6 is also schematically illustrated. Bipolar pacing of all available electrode pairs at lead 4 are tested and illustrated in the figure.

It is clearly shown from the graphs that the pacing LV electrode 7 to LV electrode 10 has the shortest time, which is indicated by "t".

By first approximating the difference in the LV electrode placement to zero compared to the distance from the LV electrodes to RV tip and RV ring the conclusion is that LV electrode 7 to LV electrode 10 also results in the highest average velocity and thus the optimal LV pacing.

Further improvement in accuracy may be achieved by taking the distances between the LV electrodes into account when determining the maximum average velocity. This means that a depolarization wave started by a pace pulse between LV electrode 9 and LV electrode 10 may have a higher velocity than a wave started between LV electrode 7 and LV electrode 8 since the former has a larger distance to cover.

However, these data are available in the memory unit and may be taken into account.

A further mean to refine the decision process is to include sensed information from for instance RA tip electrode 11 to RA ring electrode 12 or other available electrodes, e.g. RA ring electrode 12 to device housing 2.

Even if the invention is described for a quad pole on the left side of the heart the present invention is equally applicable for optimization of the pacing configuration for a multi-pole electrode in the right atrium or right ventricle.

The present invention is also applicable for any number of electrodes on the lead higher than two and/or using it for bipolar lead systems where different poles on the right and left side is used as pacing nodes and based upon determined values calculate the average velocity and thus achieving optimal pacing configurations.

It is understood that the true velocity of the depolarization wave might be equal in several of the cases shown above in connection with FIGS. 2 and 3, as some of the waves have travelled a long distance around e.g. scar tissue which makes these waves seem to have a lower velocity than it has.

However, the conclusion that the wave which appears to have the highest velocity (which might or might not by quite true) origins from the best choice of pacing electrodes is still valid.

Before the implantation of an implantable heart stimulator, an external (non-implantable) pacing device known as a pacing system analyzer (PSA) may be used to ensure adequate lead placement, maintain basic cardiac functions, and/or evaluate pacing parameters for an initial programming of the implantable pacemaker. In one example of an operation for implanting an implantable pacemaker into a patient, the patient's heart is electrically connected to the PSA through implantable sensing-pacing leads. Various pacing modes and/or parameters are evaluated to determine whether the leads are properly placed and to determine a set of suitable pacing parameters. The implantable pacemaker is then connected to the implantable sensing-pacing leads and subcutaneously implanted in the chest area. An external programmer is used to program the pacemaker via telemetry, using the set of suitable pacing parameters determined by using the PSA.

Generally, a PSA includes multiple independently controllable sensing and pacing channels. The PSA provides for a pacing system testing during an operation for implanting a pacemaker having multiple sensing and pacing channels and allows for control and adjustment of pacing parameters. The PSA may also include a display screen to visually present real-time electrograms and event markers.

Figure 5:
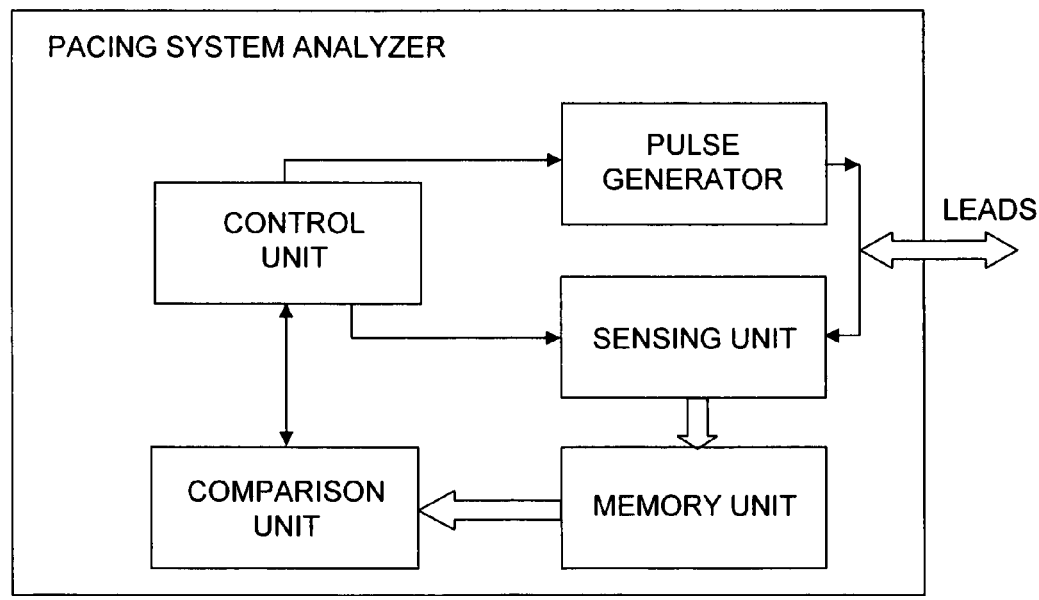
FIG. 5 is a schematic block diagram of the pacing system analyzer according to one embodiment of the present invention.

According to one embodiment of the present invention a PSA is provided with capabilities to measure and monitor the depolarization wave velocity or depolarization wave velocity measure as described above in connection with the heart stimulating device. In this embodiment the leads instead are attached to the PSA that generates the stimulation pulses and receives the electrical heart tissue responses and then performs the analysis as described above. This embodiment is schematically illustrated in FIG. 5.

Figure 6:
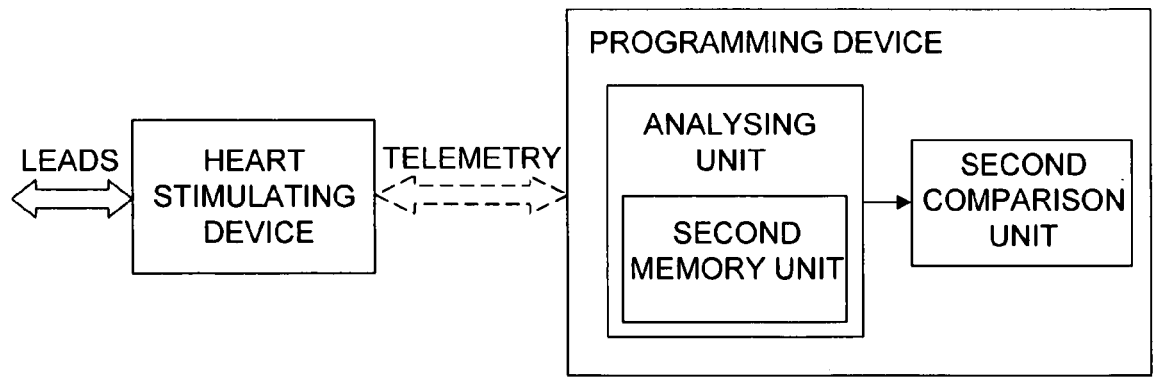
FIG. 6 is a schematic block diagram of a programming device according to one embodiment of the present invention.

According to another embodiment all, or parts, of the analysis is instead performed by an external programming device. With references to FIG. 6 the external programming device will be described. The programming device is adapted to wirelessly communicate with a heart stimulating device (indicated by a dashed double arrow), preferably of the kind described above, i.e. provided with capabilities required to determine the depolarization wave velocity or the depolarization wave velocity measure. However, within the scope of the invention as defined by the appended claims, the present invention also relates to a programming device adapted to be used for communication to and programming of an implanted heart stimulating device not provided with the above described units required to determine the depolarization wave velocities or depolarization wave velocity measures and the following analysis. According to this embodiment the programming device includes an analyzing unit provided with a second memory unit and adapted to receive sensed electrical heart tissue responses from the heart stimulating device, and that the programming device is adapted to instruct, via telemetry, the pulse generator of an implanted heart stimulating device to generate stimulation pulses to be applied to the heart tissue by different electrodes. For each of the applied pulses resulting in a depolarization wave in the heart tissue a depolarization wave velocity, or a depolarization wave velocity measure, of the wave is determined by the analyzing unit and stored in the second memory unit, and that the stored wave velocities, or velocity measures, related to different stimulating electrodes, are compared to each other in a second comparison unit and the comparison is used to adapt a stimulation mode when stimulating the heart to optimize the hemodynamic performance of the heart.

It is naturally also possible that the depolarization wave velocities, or velocity measures, are determined and stored by the heart stimulating device and that those values are submitted to the external programming device where further analysis and comparisons are performed.

In a further embodiment the invention can be implemented by a system comprising a pulse generator connected to cardiac leads and an external progammer. The pulse generator need to have a capability to transmit sensed event markers via telemetry to the programmer to allow the programmer to determine the exact point in time when a depolarisation wave has reached a particular sensing electrode. The time difference between the detection of the depolarisation wave at two different sensing electrodes can be used to determine the depolarisation wave velocity or a depolarisation wave velocity measure. The programmer will have a capability to change the electrodes used for stimulation and then determine the depolarisation wave velocity obtained for the different stimulation electrodes. The obtained depolarisation wave velocities or depolarisation wave velocity measures are stored in the programmer's memory and a comparison of stored depolarisation wave velocities or measures can be done to determine a stimulation mode when when stimulating the heart in order to optimize the hemodynamic performance of the heart. The most optimal stimulation mode may be the one the results in the highest depolarisation wave velocity or the highest depolarisation wave velocity measure. The change to a more optimal stimulation mode can either be manually initiated by a physician or automatic. The change of stimulation mode may be a change of stimulation electrode.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A heart stimulating system comprising:
   an implantable device having a stimulation pulse generator adapted to generate stimulation pulses,
   a stimulation lead coupled to said pulse generator, the stimulation lead having a plurality of stimulation and sensing electrodes;
   a sensing unit adapted to sense electrical heart tissue responses via said sensing electrodes to electrical stimulation pulses applied via said stimulation electrodes, the sensing unit being adapted to determine a depolarization wave velocity parameter for each stimulation pulse that results in a depolarization wave;
   a memory unit coupled to the sensing unit and adapted to store the depolarization wave velocity parameters as a function of the plurality of stimulation electrodes,
   a comparison unit adapted to compare the stored wave velocity parameters related to different ones of the plurality of stimulation electrodes wherein the comparison is used to adapt a stimulation electrode configuration when stimulating the heart to optimize the hemodynamic performance of the heart.

2. The system according to claim 1, wherein the stimulation mode is adapted by changing the electrode configuration.

3. The system according to claim 2, wherein the electrode that provided the highest depolarization wave velocity is chosen in order to adapt the electrode configuration.

4. The system according to claim 1, wherein said depolarization wave velocity parameter is used to monitor the hemodynamic performance of the heart.

5. The system according to claim 1, wherein the depolarization wave velocity parameter is measured at electrodes not used for stimulation.

6. The system according to claim 1, wherein the wave velocity is measured by determining the distance between the used stimulation electrode and the used sensing electrode and dividing the distance with the time period from applied stimulation until the wave reaches the sensing electrode.

7. The system according to claim 1, wherein the wave velocity parameter is a time measure determined by measuring the time from applied stimulation until the wave reaches the used sensing electrode.

8. The system according to claim 1, wherein the electrodes are adapted to operate in a unipolar configuration.

9. The system according to claim 1, wherein the electrodes are adapted to operate in a bipolar configuration.

10. The system according to claim 1, wherein said device being adapted to be connected to a left ventricular multi electrode lead adapted to stimulate the left ventricle of the heart.

11. The system according to claim 1, wherein the device comprises a control unit adapted to initiate determination of the optimal electrode configuration at predetermined time intervals.

12. The system according to claim 1, wherein the device comprises a control unit adapted to initiate determination of the optimal electrode configuration when receiving an initiation signal.

13. The system according to claim 1, wherein the control unit is adapted to monitor changes of depolarization wave velocities, which may be used to detect adverse changes in the patient's hemodynamic status.

14. The system according to claim 1, wherein if a monitored velocity change is detected then the device automatically determines if an alternative electrode configuration instead may be used, or an alarm signal is generated and transmitted to an external device.

15. The system according to claim 1, wherein said heart stimulating device is implantable.

16. The system according to claim 1, wherein said heart stimulating device is a pacing system analyzer (PSA).

17. The system according to claim 1, further comprising:
    a programming device adapted to wirelessly communicate with the implantable device, wherein the programming device includes
    an analyzing unit provided with a second memory unit and adapted to receive sensed electrical heart tissue responses from the implantable device, and that the programming device is adapted to instruct the pulse generator to generate stimulation pulses to be applied to the heart tissue by different ones of the plurality of stimulation electrodes.

18. A system comprising:
    a stimulation pulse generator arranged in a stimulator housing,
    a programming device adapted to wirelessly communicate with the stimulation pulse generator,
    one or more leads having a plurality of stimulation and sensing electrodes, the one or more leads coupled to the stimulation pulse generator, wherein the stimulation pulse generator is coupled to the plurality of stimulating and sensing electrodes;
    a sensing unit adapted to sense electrical tissue responses via said sensing electrodes to electrical stimulation pulses applied via said stimulating electrodes,
    said programming device being adapted to order the pulse generator to generate stimulation pulses to be applied to the heart tissue by different ones of the plurality of stimulating electrodes, said pulse generator being adapted to transmit telemetry markers indicating to the programming device when a depolarization wave has been sensed at a sensing electrode,
    said programming device being further adapted to determine a depolarization wave velocity parameter as a function of the time at which the depolarization wave reached the sensing electrodes,
    said programmer being further adapted to store said depolarization wave velocity parameters related to the different stimulating electrodes,
    said programming device being adapted to compare the stored depolarization wave velocity parameters to each other, and to adapt the stimulation electrode configuration when stimulating the heart to optimize the hemodynamic performance of the heart as a function of the comparison.

19. The system according to claim 18, wherein the stimulation mode is adapted by changing the stimulation electrode configuration.

20. The system according to claim 19 wherein the stimulation electrode configuration is selected that gives the highest depolarization wave velocity parameter.

* * * * *